US010215690B2

(12) United States Patent
Craddock et al.

(10) Patent No.: US 10,215,690 B2
(45) Date of Patent: Feb. 26, 2019

(54) METHOD FOR ESTIMATING A VALUE OF A KEROGEN PROPERTY IN SUBSURFACE FORMATIONS

(71) Applicant: Schlumberger Technology Corporation, Sugar Land, TX (US)

(72) Inventors: Paul Ryan Craddock, Scituate, MA (US); Michael David Prange, Somerville, MA (US); Andrew Emil Pomerantz, Lexington, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 15/398,399

(22) Filed: Jan. 4, 2017

(65) Prior Publication Data

US 2018/0188161 A1 Jul. 5, 2018

(51) Int. Cl.
*G01N 21/35* (2014.01)
*G01N 33/28* (2006.01)

(52) U.S. Cl.
CPC ............ *G01N 21/35* (2013.01); *G01N 33/28* (2013.01)

(58) Field of Classification Search
CPC ............................... G01N 21/35; G01N 33/28
See application file for complete search history.

(56) References Cited

U.S. PATENT DOCUMENTS 4,321,465 A 3/1982 Stover et al.
5,306,909 A * 4/1994 Jones ................ G01N 21/3577 250/255
8,906,690 B2 12/2014 Pomerantz
2009/0187391 A1* 7/2009 Wendt ...................... G01V 1/28 703/7
2013/0269933 A1 10/2013 Pomerantz et al.
2013/0273661 A1 10/2013 Pomerantz
2015/0323516 A1* 11/2015 Washburn ............ G06F 19/703 436/32
2016/0084756 A1 3/2016 Herron et al.
(Continued)

FOREIGN PATENT DOCUMENTS

WO 2014022757 A1 2/2014

OTHER PUBLICATIONS

Behar, F. et al., "Rock-Eval 6 Technology: Performances and Developments", Oil & Gas Science and Technology—Reviews I.F.P., 2012, 56(2), pp. 111-134.

(Continued)

*Primary Examiner* — David P Porta
*Assistant Examiner* — Faye Boosalis

(57) ABSTRACT

A method for estimating a value of a kerogen property in a subsurface formation where the value of the kerogen property is unknown. The method includes: measuring spectral intensity values over an infrared (IR) spectral range for a selected sample from the subsurface formation; determining a range of values representing the measured spectral intensity values corresponding to a vibrational mode attributable to kerogen in the selected sample, the range of values including values representing uncertainty in the measured spectral intensity over the portion of the spectral range; and inputting values from the range of values into a stochastic or simple regression model to determine an estimated value of the kerogen property in the selected sample.

26 Claims, 8 Drawing Sheets

(56) References Cited

U.S. PATENT DOCUMENTS

2017/0248011 A1 8/2017 Craddock et al.
2018/0202906 A1 7/2018 Loan et al.

OTHER PUBLICATIONS

Chen, Y. et al., "Characterization of chemical functional groups in macerals across different coal ranks via micro-FTIR spectroscopy", International Journal of Coal Geology, 2012, 104, pp. 22-33.

Craddock, P. R. et al., "Evolution of kerogen and bitumen during thermal maturation by semi-open pyrolysis investigated by infrared spectroscopy", Energy & Fuels, 2015, 29, pp. 2197-2210.

Ganz, H. et al., "Application of infrared spectroscopy to the classification of kerogen—types and the evaluation of source rock and oil shale potentials", 1987 Fuel, 66(5), pp. 708-711.

Guo, Y. et al., "Micro-FTIR spectroscopy of liptinite macerals in coal", International Journal of Coal Geology, 1998, 36(3-4), pp. 259-275.

Hackley, P. C. et al., "Standardization of reflectance measurements in dispersed organic matter: Results of an exercise to improve interlaboratory agreement", 2015, Marine and Petroleum Geology, 59, pp. 22-34.

Ibarra, J. V. et al., "FTIR study of the evolution of coal structure during the coalification process", Organic Geochemistry, 1996, 24(6-7), pp. 725-735.

Lin, R. et al., "Studying individual macerals using i.r. microspectroscopy, and implications on oil versus gas/condensate proneness and "low-rank" generation", Organic Geochemistry, 1993, 20(6), pp. 695-706.

Lis, G. P. et al., "FTIR absorption indices for thermal maturity in comparison with vitrinite reflectance Ro in type-II kerogen from Devonian black shales", Organic Geochemistry, 2005, 36(11), pp. 1533-1552.

Painter, P. C. et al., "Concerning the Application of FT-IR to the Study of Coal: A Critical Assessment of Band Assignments and the Application of Spectral Analysis Programs", Applied Spectroscopy, 1981 35(1), pp. 475-485.

Tissot, B. et al., "Geochemical study of the Uinta Basin: formation of petroleum from the Green River formation", Geochimica et Cosmochimica Acta, 1978, 42(10), pp. 1469-1485.

International Search Report and Written Opinion for corresponding PCT Application Serial No. PCT/US2018/012125, dated May 10, 2018, 21 pages.

Chen, Y. et al., "Application of Micro-Fourier Transform Infrared Spectroscopy (FTIR) in the Geological Sciences", International Journal of Molecular Sciences, Dec. 18, 2015, vol. 16, pp. 30223-30250.

* cited by examiner

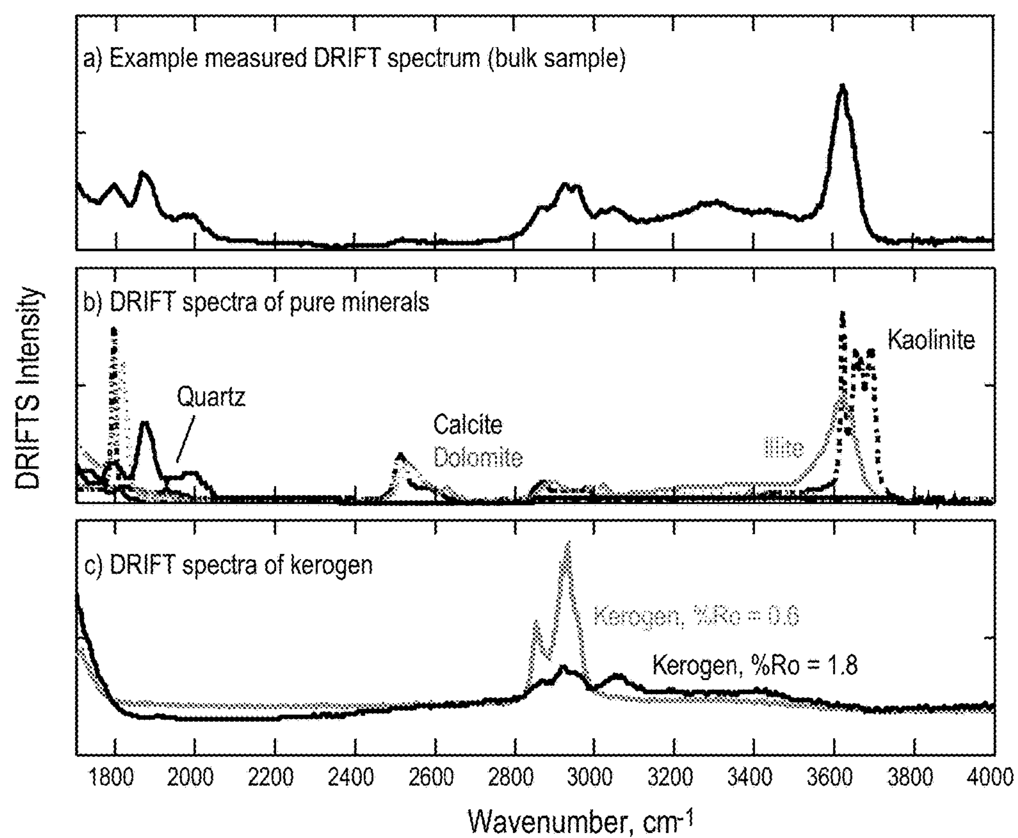
Prior Art

METHOD FOR ESTIMATING A VALUE OF A KEROGEN PROPERTY IN SUBSURFACE FORMATIONS

FIELD OF THE DISCLOSURE

The present invention is directed to the evaluation of petroleum source rocks, and more specifically to a method for estimating a value of a property of organic matter in subsurface formations.

BACKGROUND

Formation evaluation in petroleum source rocks (commonly referred to as shales) involves estimating petrophysical parameters of the organic matter in the rock formations, such as its thermal maturity and density. The organic matter here refers to the dispersed, solid, and insoluble organic matter in sedimentary rocks termed kerogen. Thermal maturity is important for evaluating reservoir quality, hydrocarbon quality, and hydrocarbon type. The density (specifically grain or skeletal density) of kerogen is important for estimating porosity. The measurement of kerogen properties (e.g., thermal maturity and density) as a function of depth is desirable in nearly every well drilled in a petroleum source rock.

In general, kerogen properties are determined from time-consuming and expensive laboratory techniques. For example, thermal maturity of kerogen has been estimated using vitrinite reflectance, in which the optical reflectance of vitrinite macerals in kerogen immersed under oil is estimated and expressed as vitrinite reflectance maturity (see Hackley, P. et al., Standardization of reflectance measurements in dispersed organic matter: Results of an exercise to improve interlaboratory agreement. Marine and Petroleum Geology, 59, 22-34 (2015).) An alternative laboratory technique for estimating thermal maturity is using programmed pyrolysis (see Behar, F. et al., Rock-Eval 6 Technology: Performances and Developments. Oil & Gas Science and Technology—Reviews I.F.P., 56(2), 111-134 (2001)) by measuring the temperature at which maximum decomposition of kerogen ($T_{max}$) occurs and then calculating vitrinite reflectance from known correlations between $T_{max}$ and vitrinite reflectance. More recently, attempts have been made to correlate the thermal maturity to vibrational modes obtained by infrared (IR) spectroscopy. For the purposes of describing the invention herein, thermal maturity is quantified in terms of vitrinite reflectance units, % Ro, which is the scale upon which vitrinite reflectance measurements are quantified. Other scales for thermal maturity are known to those skilled in the art. With respect to kerogen density, determinations are typically made using gas pycnometry techniques known to those of ordinary skill in the art. The measurements are made on kerogen isolated from the bulk formation sample, which requires hazardous laboratory treatment of the sample with series of concentrated acids such as HCl, HF, and sometimes $CrCl_2$, to dissolve inorganic minerals including silicates, aluminosilicates, carbonates, and metal sulfides, among others, and yielding a kerogen concentrate free of inorganic phases.

The infrared (IR) spectrum of kerogen varies as a function of its composition and structure. IR spectroscopy measurements respond directly to the type and abundance of molecular bonds, e.g., structure, in the material being studied. Therefore, IR spectroscopy may provide information on certain kerogen properties. Several structural indices for kerogen have been defined on the basis of IR spectroscopy measurements and several of these have been correlated to thermal maturity (see Chen, Y., et al., Characterization of chemical functional groups in macerals across different coal ranks via micro-FTIR spectroscopy. International Journal of Coal Geology 104, 22-33 (2012); Craddock, P. R., et al., Evolution of kerogen and bitumen during thermal maturation by semi-open pyrolysis investigated by infrared spectroscopy. Energy & Fuels 29, 2197-2210 (2015); Ganz, H., et al., Application of infrared spectroscopy to the classification of kerogen-types and the evaluation of source rock and oil shale potentials. Fuel 66, 708-711 (1987); Guo, Y., et al., Micro-FTIR spectroscopy of liptinite macerals in coal. International Journal of Coal Geology 36, 259-275 (1998); Ibarra, J. V., et al., FTIR study of the evolution of coal structure during the coalification process. Organic Geochemistry 24, 725-735 (1996); Iglesias, M., et al., FTIR study of pure vitrains and associated coals. Energy & Fuels 9, 458-466 (1995); Lin, R., et al., Studying individual macerals using IR microspectroscopy, and implications on oil versus gas/condensate proneness and "low-rank" generation. Organic Geochemistry 20, 697-706 (1993); Lis, G. P., et al., FTIR absorption indices for thermal maturity in comparison with vitrinite reflectance Ro in type-II kerogen from Devonian black shales. Organic Geochemistry 36, 1533-1552 (2005); Painter, P. C., et al., Concerning the application of FTIR to the study of coal: A critical assessment of band assignments and the application of spectral analysis programs. Applied Spectroscopy 35, 475-485 (1981); Tissot, B., et al., Geochemical study of the Uinta Basin: formation of petroleum from the Green River formation. Geochimica et Cosmochimica Acta 42, 1469-1485 (1978).)

Structural indices for estimating thermal maturity have been developed by quantifying one or more of the following IR absorption bands: aromatic CH out-of-plane deformation (about 700-900 $cm^{-1}$), aliphatic $CH_3$ symmetric deformation (about 1375 $cm^{-1}$), aliphatic $CH_2$ symmetric deformation (about 1450 $cm^{-1}$), aliphatic $CH_3$ antisymmetric deformation (about 1460 $cm^{-1}$), aromatic C=C stretches (about 1600 $cm^{-1}$), oxygenated (carboxyl and carbonyl) stretches (about 1650-1770 $cm^{-1}$), aliphatic $CH_2$ and $CH_3$ symmetric and antisymmetric stretches (about 2800-3000 $cm^{-1}$), and aromatic CH stretches (about 3000-3100 $cm^{-1}$).

Most of the structural indices derived to date are limited to the measurement of kerogen isolated from the surrounding rock (mineral) matrix, because most organic IR absorption bands (those below 1800 $cm^{-1}$) are otherwise obscured by more intense IR absorption bands associated with inorganic minerals. IR absorption bands associated with kerogen between about 2800 and about 3100 $cm^{-1}$ are readily amenable to study in bulk samples. Therefore, art based on the IR analysis of isolated kerogens is not necessarily useful or applicable to rapid measurement of bulk formation samples.

Methods exist to estimate the thermal maturity of kerogen in bulk formation samples using IR spectroscopy, for example, as described in U.S. Pat. No. 8,906,690, which is hereby incorporated by reference in its entirety. These methods are based on spectral deconvolution and curve fitting of measured IR spectral features between 2800 and 3000 $cm^{-1}$ related to absorption bands of the following vibrational modes: (i) a $CH_2$ symmetric stretch centered at about 2849 $cm^{-1}$, (ii) a $CH_3$ symmetric stretch centered at about 2864 $cm^{-1}$, (iii) a CH stretch centered at about 2891 $cm^{-1}$, (iv) a $CH_2$ antisymmetric stretch centered at about 2923 $cm^{-1}$, and (v) a $CH_3$ antisymmetric stretch centered at about 2956 $cm^{-1}$ to obtain an estimate of a $CH_2/CH_3$ ratio in kerogen, wherein the ratio is indicative of thermal maturity.

Methods exist to estimate the density of kerogen in bulk formation samples from IR spectroscopy, for example, as described in U.S. patent application Ser. No. 15/053,604, Methods for improving matrix density and porosity estimates in subsurface formations by Craddock, P. R., et al, the contents of which are hereby incorporated by reference in its entirety. These methods are also based on spectral deconvolution and curve fitting of measured IR spectral features between 2800 and 3000 $cm^{-1}$, described generally above.

The spectral deconvolution and curve fitting techniques used depend on parameters such as the type of function used (e.g., Gaussian, Lorentzian, Voight, etc.), the number of curves to be solved, the peak centers of the curves, and the widths of the curves, not all of which are known.

BRIEF SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method for estimating a value of a kerogen property in a subsurface formation where the value of the kerogen property is unknown. The method includes: measuring spectral intensity values over an infrared (IR) spectral range for a selected sample from the subsurface formation; determining a range of values representing the measured spectral intensity values corresponding to a vibrational mode attributable to kerogen in the selected sample, the range of values including values representing uncertainty in the measured spectral intensity over the portion of the spectral range; and inputting values from the range of values into a stochastic regression model to determine an estimated value of the kerogen property in the selected sample.

A method for estimating a value of a kerogen property in subsurface formation where the value of the kerogen property is unknown. The method includes: measuring spectral intensity values over an infrared (IR) spectral range for a selected sample from the subsurface formation; determining a value representing the measured spectral intensity value over a portion of the spectral range corresponding to a vibrational mode attributable to kerogen in the selected sample; and inputting the value into a regression model to determine the estimated value of the kerogen property in the selected sample.

A method for estimating a value of a kerogen property in a subsurface formation, the value of the kerogen property is unknown. The method includes: measuring spectral intensity values over an infrared (IR) spectral range for a selected sample from the subsurface formation; determining a first value representing the measured spectral intensity values corresponding to a first vibrational mode attributable to kerogen in the selected sample, the first vibrational mode is an aromatic CH stretch; and inputting the first value into a regression model to determine the estimated value of the kerogen property in the selected sample.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIG. 1*a* illustrates an infrared (IR) spectrum of a shale sample obtained using Diffuse Reflectance Infrared Fourier Transform Spectroscopy (DRIFTS) over a spectral range of 1700 $cm^{-1}$ to 4000 $cm^{-1}$;

FIG. 1*b* illustrates IR spectra for pure minerals obtained using DRIFTS over a spectral range of 1700 $cm^{-1}$ to 4000 $cm^{-1}$;

FIG. 1*c* illustrates IR spectra of two kerogens obtained by removing the IR contributions of pure minerals (illustrated in FIG. 1*b*) from their respective bulk formation samples (one example spectrum from a bulk formation sample is given in FIG. 1*a*.);

in FIG. 2*b*) of kerogen and thermal maturity as determined using vitrinite reflectance for samples having a range of thermal maturities;

in FIG. 2*b*) of kerogen and densities as determined using gas pycnometry for samples having a range of densities;

FIG. 7*b* is a comparison of thermal maturity determined using vitrinite reflectance measurements to that estimated from the $CH_3/CH_2$ ratio from published curve fitting techniques;

FIG. 8*b* is a comparison of kerogen densities determined using gas pycnometry measurements to that estimated from the $CH_3/CH_2$ ratio from published curve fitting techniques.

DETAILED DESCRIPTION

Figures 2A, 2B:
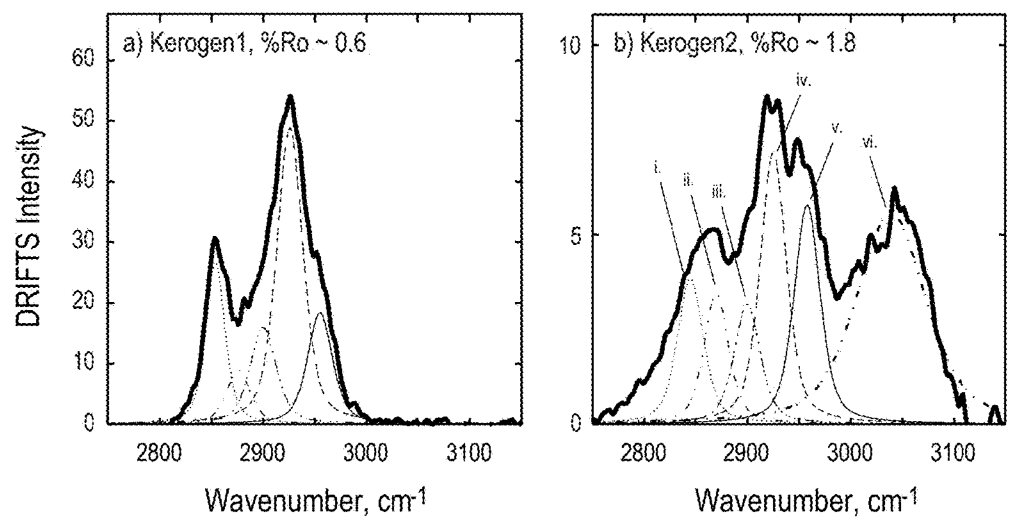
FIGS. 2*a* and 2*b* illustrate IR spectra of kerogen components of shale samples obtained by DRIFTS over a spectral range of about 2800 $cm^{-1}$ to 3100 $cm^{-1}$.

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Conventional methods do not provide a measure of uncertainty in the estimation of kerogen properties (such as thermal maturity and density), which makes decisions on whether to finance a drilling project more difficult. Further, the IR spectrum of kerogen should allow for simultaneous or alternative estimation of other kerogen properties that are related to its composition and structure, which are not considered in conventional methods. The subject disclosure relates to improved methods for estimating kerogen properties in subsurface formations.

A method for estimating a value of a kerogen property, such as its thermal maturity and density, in a subterranean rock formation is described herein. The method advantageously removes the need for expensive, time-consuming, laboratory methods to estimate these kerogen properties in a sample where the value of the kerogen property is unknown. The method may use at least one vibrational mode obtained from IR spectroscopy of a sample of the rock formation. The method may use at least three vibrational modes in some embodiments. The method may determine a range of values for the estimated kerogen property, wherein the range of values including values representing uncertainty in the estimated property. Uncertainty provides a better understanding of the kerogen property in a given subterranean formation and may remove certain risks when considering whether to finance a drilling project at the subterranean formation in question.

Sample Collection

As discussed herein, a subterranean sedimentary formation may comprise sedimentary organic matter (termed kerogen) and may further comprise inorganic minerals. Samples from such a formation may be drill core, drill cuttings, outcrop, etc. If drill cuttings are collected, the drilling mud should be removed. Relevant sample collection and preparation procedures are described in U.S. patent application Ser. No. 13/446,985, filed Apr. 13, 2012, and U.S. Pat. No. 8,906,690, the disclosures of which are hereby incorporated herein by reference.

There are two types of samples collected. First, a set of samples that will be used to develop the model discussed herein. These samples may be selected to have a broad range in thermal maturity and/or density such that a more accurate model can be developed. For example, it is known that thermal maturity in petroleum source rocks can range on the vitrinite reflectance scale from at least about 0.3% Ro to about 5.0 Ro and that the density of kerogen can range from at least about 1.0 g/cm$^3$ to about 1.6 g/cm$^3$. This set of samples will be measured using IR spectroscopy and some other independent method for quantifying the kerogen property of interest. This includes one or more of: thermal maturity, such as by using vitrinite reflectance or programmed pyrolysis; and density, such as by using gas pycnometry. As such, each sample in this set of samples will have known values for the one or more kerogen properties of interest. Second, samples having unknown values of one or more kerogen properties of interest will be collected. These samples will be obtained from a wellbore, drilling site, prospective drilling site, and measured using IR spectroscopy. From the information obtained from IR spectroscopy, the model developed herein will be used to estimate the value of the one or more kerogen properties of interest in those samples.

Data Collection

A collected sample is measured using IR spectroscopy. The measurement can be made using any measurement mode, such as transmission, diffuse reflectance, attenuated total reflectance, etc. Unless otherwise noted, the IR spectra discussed herein were acquired using diffuse reflectance infrared Fourier transform spectroscopy (DRIFTS). The measured spectral range may be in the mid-infrared between about 400 and about 4000 cm$^{-1}$. However, smaller spectral ranges could be utilized, for example, about 2800 to about 3200 cm$^{-1}$.

One spectrum for a collected shale sample is depicted in FIG. 1*a*. This spectrum includes IR contributions from kerogen and from minerals that absorb in the spectral range measured. Minerals include quartz, calcite, dolomite, illite, and kaolinite. IR spectra for pure minerals are depicted in FIG. 1*b*. The IR spectra depicted in FIG. 1*b* is not from a collected shale sample, but from separately measured IR spectra of each mineral identified in FIG. 1*b*. As will be readily apparent to one of ordinary skill in the art, spectral features associated with these pure minerals are present in the IR spectrum of the collected sample depicted in FIG. 1*a*. Although it is not required, in some embodiments, removal of the IR contributions attributed to these pure minerals may improve the maturity estimate. Two such IR spectra where the IR contributions attributed to pure minerals are removed are depicted in FIG. 1*c*. Upon removal of the IR contributions attributed to these pure minerals, the IR contributions for kerogen remain in the IR spectrum. Optionally, other modifications to the IR spectrum can be made, such as baseline correction using fitting procedures known in the art, such as linear, polynomial, or the like to obtain a flat baseline.

A collected sample is measured for a kerogen property. One property that may be measured is thermal maturity. A common technique to estimate thermal maturity is vitrinite reflectance (Hackley, P. et al. Standardization of reflectance measurements in dispersed organic matter: Results of an exercise to improve interlaboratory agreement. Marine and Petroleum Geology, 59, 22-34 (2015).). In this method, a polished surface of a formation sample immersed in oil is examined under high magnification using white light. The reflectance of light from vitrinite or other macerals of kerogen in the sample is measured and recorded as percent reflectance (% Ro) relative to standards of known reflectance. Other methods to determine thermal maturity, include programmed pyrolysis. Any method to independently estimate thermal maturity can be used to build the model. It is convenient, although not necessary, to quantify thermal maturity measurements in vitrinite reflectance units.

Another kerogen property that may be measured is kerogen density. A technique to estimate kerogen density is gas expansion pycnometry. In this method, the volume of a known mass of kerogen is measured using gas displacement and a known volume-pressure relationship. The density of kerogen is computed from the known mass and measured volume using the density equation: mass is equal to density multiplied by volume, with compatible units.

Determining One or More Values Representing IR Contributions Attributed to Kerogen The methods discussed herein are used to determine a value representing the IR contributions attributed to kerogen for both the set of collected samples with known kerogen properties used to develop the model, and collected samples having unknown kerogen properties, which can be determined from the model.

Conventional Methods

Conventional methods of determining a value representing IR contributions attributed to kerogen are depicted in FIG. 2*a-b*, which depict IR spectra from collected samples of known and different kerogen properties such as, for example, thermal maturity. The collected sample depicted in FIG. 2*a* has lower thermal maturity (0.6% Ro) than that depicted in FIG. 2*b* (1.8% Ro). For these samples, the thermal maturities in each collected sample were determined using vitrinite reflectance. The spectral features attributable to kerogen over the spectral range of about 2800 $cm^{-1}$ to about 3100 $cm^{-1}$ are comprised of up to six principal vibrational modes. The six principal modes are: i. $CH_2$ symmetric stretch, ii. $CH_3$ symmetric stretch, iii. CH stretch, iv. $CH_2$ antisymmetric stretch, v. $CH_3$ antisymmetric stretch, and vi. aromatic CH stretch. As depicted in FIGS. 2*a-b*, the shape of the IR spectrum (i.e., the relative amplitudes of the peaks associated with principal modes) differs because the relative abundance of methyl ($CH_3$), methylene ($CH_2$), and aromatic CH structural groups in kerogen vary systematically as a function of thermal maturity.

Figure 3A:
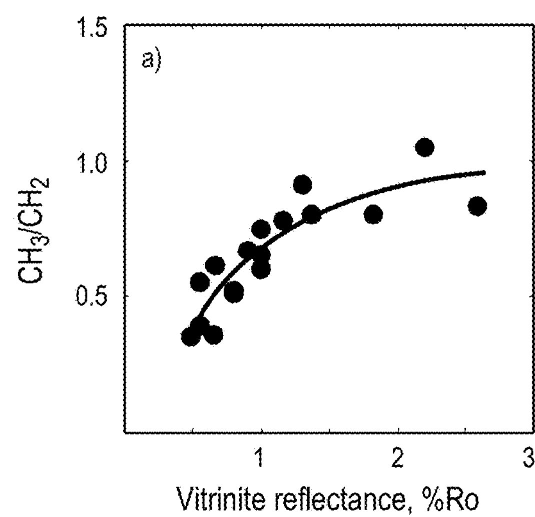
FIG. 3*a* is a graph illustrating a correlation between a $CH_3/CH_2$ ratio obtained from IR spectra for kerogen components and thermal maturities as determined using vitrinite reflectance for samples having a range of thermal maturities.
Figure 3B:
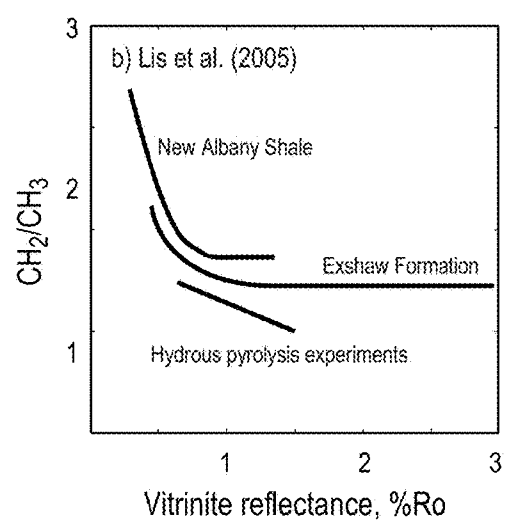
FIG. 3*b* is a graph similar to FIG. 3*a*, but illustrates the correlation between the inverse ratio $CH_2/CH_3$ and thermal maturity for a different set of samples.
Figure 4:
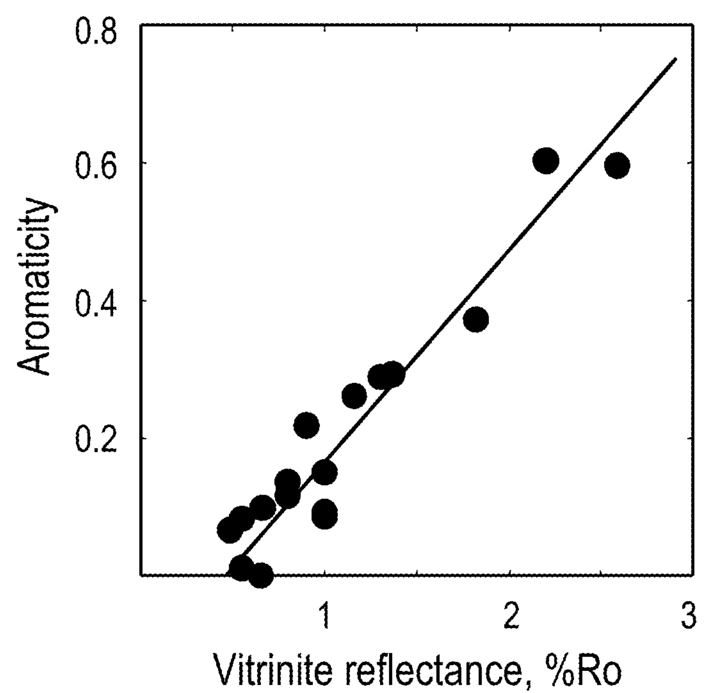
FIG. 4 is a graph illustrating a correlation between the ratio of the area of the aromatic CH stretch vibrational mode (curve vi in FIG. 2*b*) to the area of all the vibrational modes (curves i.—vi.
Figure 5A:
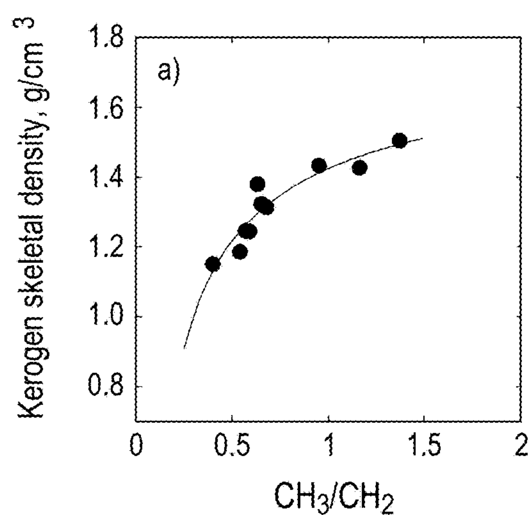
FIG. 5*a* is a graph illustrating a correlation between a $CH_3/CH_2$ ratio obtained from IR spectra for kerogen components and densities as determined using gas pycnometry for samples having a range of densities.
Figure 5B:
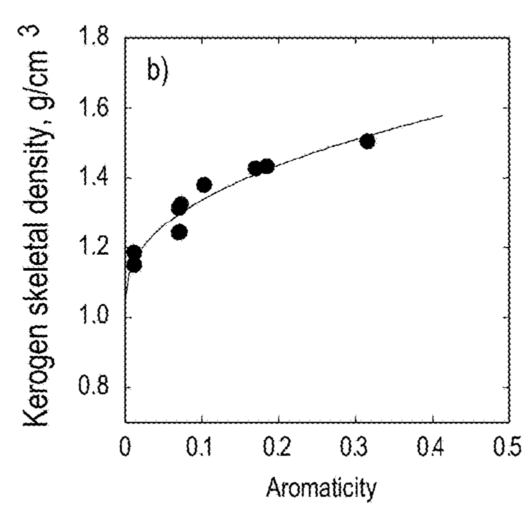
FIG. 5*b* is a graph illustrating a correlation between the ratio of the area of the aromatic CH stretch vibrational mode (curve vi in FIG. 2*b*) to the area of all the vibrational modes (curves i.—vi.

A value of a kerogen property estimated from IR spectroscopy is based on the concept that these principal vibrational modes vary predictably with the value of the kerogen property. For example, FIG. 3*a* shows how the $CH_3/CH_2$ ratio of kerogen in a diverse set of organic-rich mudstones increases with thermal maturity. FIG. 3*a* is obtained, for example, by separately determining both thermal maturity (here by vitrinite reflectance) and an IR spectrum for a given collected sample, and then plotting their correlation. FIG. 3*b* shows the same trend plotted as the inverse ratio $CH_2/CH_3$ of organic matter for a different set of organic-rich mudstones published in Lis, G. P., et al., FTIR absorption indices for thermal maturity in comparison with vitrinite reflectance Ro in type-II kerogen from Devonian black shales. Organic Geochemistry 36, 1533-1552 (2005). The $CH_3/CH_2$ ratio or its inverse in FIGS. 3*a*-b plateau at thermal maturities above about 1.5% Ro. FIG. 4 shows how a different IR structural index, namely aromaticity, correlates with thermal maturity. Here, aromaticity is defined as the ratio of the area of the aromatic CH stretch (i.e., curve vi in FIG. 2*b*) to the total area of all five aliphatic CH stretches plus the aromatic CH stretch (i.e., curves i-vi in FIG. 2*b*). However, other definitions of aromaticity could be utilized. FIG. 5*a*-b similarly shows how the $CH_3/CH_2$ ratio and aromaticity of kerogen in a different set of organic-rich mudstones correlates to another kerogen property, namely kerogen skeletal density, as shown in Craddock P. R., et al. Methods for improving matrix density and porosity estimates in subsurface formations, U.S. patent application Ser. No. 15/053,604, the contents of which are herein incorporated by reference.

The conventional methods using deconvolution and curve fitting of the kerogen spectra depicted in FIG. 2*a-b* to obtain IR structural indices (e.g., $CH_3/CH_2$ ratio, aromaticity) are subject to uncertainties because the accuracy of the curve fitting technique is dependent upon several parameters including the functional form of the curve fitting (e.g., Gaussian, Lorentzian, Voigt, etc.), the number of curves to be solved, the peak centers of the curves, and the widths of the curves. Not all of these parameters are known a priori. Moreover, the spectral deconvolution is typically done in such a way that the fitting of one curve is directly related to the fitting of other curve, such that an error or poor fit to one vibrational mode can give rise to errors or poor fits in the other vibrational modes. Accordingly, a new method of spectral interpolation is proposed herein.

New Methods of Spectral Interpolation

Figure 6:
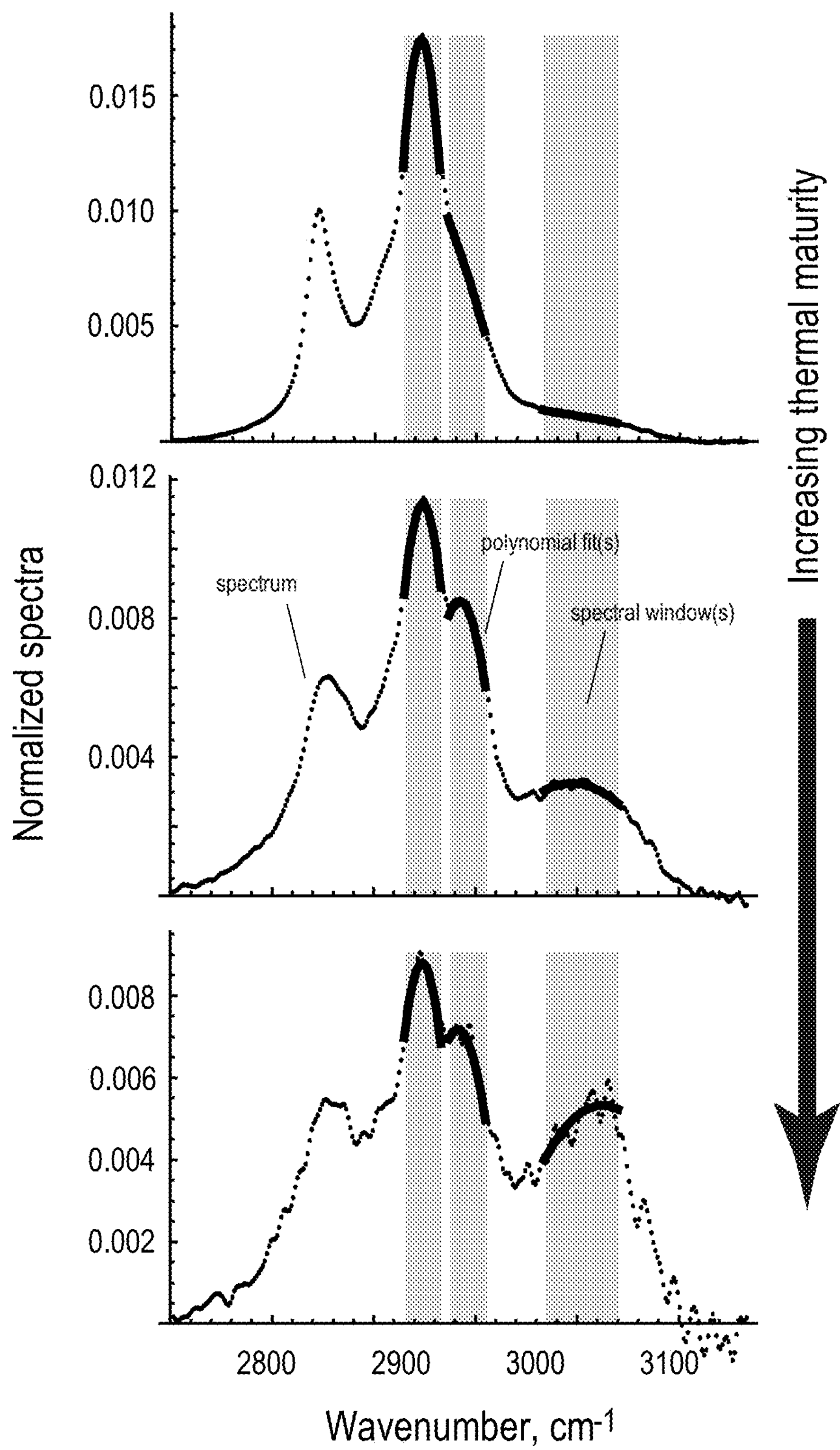
FIG. 6 illustrates IR spectra of the kerogen component of three different formation samples having increasing thermal maturity from top to bottom. The measured spectral features (black dotted line) representing different vibrational modes of a kerogen component are fitted over spectral windows (shaded gray areas) using a polynomial function (black solid line)

FIG. 6 depicts normalized IR spectra of collected samples over a spectral range of about 2800 $cm^{-1}$ to about 3100 $cm^{-1}$. For illustrative purposes, the samples are shown in order of increasing thermal maturity from the top graph to the bottom graph as can be seen by the emergence of the aromatic CH stretch vibrational mode between about 3000 $cm^{-1}$ and about 3100 $cm^{-1}$. The measured IR spectral intensity values are depicted by black dots. A spectral window, e.g., a portion of the spectral range, (grayscale shaded area) can be defined to represent each principal vibrational mode that is being fit. Any number of spectral windows can be used for the spectral interpolation. In some embodiments, one window is used. In other embodiments, more than one window is used. For illustrative purposes, in FIG. 6, spectrum windows are defined for the $CH_2$ antisymmetric stretch, the $CH_3$ antisymmetric stretch, and the aromatic CH stretch, respectively. The spectral range of each window can be defined, for example, by maximizing the width of each window representing the selected vibrational mode while simultaneously avoiding overlap and interference from adjacent vibrational modes. The spectral interpolation is relatively insensitive to the chosen width of each window within several wavenumbers more or less of the windows illustrated in FIG. 6.

Once the spectral window has been defined for each vibrational mode, a polynomial function (black solid curves in FIG. 4) is fit to the measured spectrum within that window. The degree of the polynomial function used in fitting is not particularly limited, and can be selected such that it provides the best fit to the measured IR spectral intensity values within each spectrum window. For example, each spectral window could be fitted with the same degree of polynomial, or polynomials of different degree depending on which provides the best fit to the measured IR spectral intensity values within that spectral window. For the spectral interpolations shown in FIG. 6, a fit of the measured spectral intensity values to a polynomial function in each spectral window is independent of the fits in the other spectral windows. This is a difference in the method of spectral interpolation described herein from conventional methods, such as illustrated in FIG. 2, for which the polynomial fits (curves) representing each vibrational mode are highly dependent upon the adjacent fits representing the other vibrational modes.

From each polynomial function in the spectral interpolation, a value can be obtained that represents the vibrational mode. For example, one way of obtaining a value that represents a given vibrational mode is to use the value of the polynomial function at the midpoint of the spectral window. For example, in the top graph of FIG. 6, the midpoint value of the polynomial function for the $CH_2$ antisymmetric stretch is approximately the maximum of the fitted polynomial function, while it is approximately the midpoint of the linear-shaped polynomial function for the $CH_3$ antisymmetric stretch in the same graph. However, for the $CH_3$ antisymmetric stretch in the middle graph of FIG. 6, the midpoint value of the polynomial function is approximately the maximum of the polynomial function. Obtaining a value of the polynomial function at the midpoint of the spectrum window is one way of representing each vibrational mode. Other representations are possible, such as a value at a different defined wavenumber in each of the spectral windows (meaning at a value other than the midpoint as discussed herein), by computing the mean value of each of the polynomial functions, or by computing the sum area under the spectrum within each spectral window, or the like. However, a consistent representation should be utilized. For example, if the value of a polynomial function at the midpoint of the spectrum window is selected as the representation of the vibrational mode, then this representation should be used for all spectral windows.

In the case that the spectral interpolation further includes estimates of uncertainty, referred to here as stochastic modeling, the value representing a vibrational mode can be a range of values. One range of values may be a distribution function. During stochastic modeling, a random number from the values in the range of values can be selected. For example, a range of values, where the range of values includes values representing uncertainty in the measured spectral intensity over the spectral window can be obtained for each vibrational mode in FIG. 6. The range of values may be based on the polynomial function and a difference between the measured IR spectral intensity values and the values of polynomial function within each spectral window. For example, the range of values representing a given vibrational mode can be computed by using a value of the polynomial function at the midpoint of the spectral window as a mean value, and the standard deviation between the measured IR spectral intensity values and the values of the polynomial function over the spectral window, to represent the mean value and standard deviation in a distribution function, such as a Gaussian distribution, i.e., an normal distribution. Computation of the standard deviation is known in the art, and can be computed by taking the sum of the squares of the residual, dividing by the total number of points to get a value, and then taking the square root of that value.

Similarly, when stochastic modeling is used as discussed herein, the measured value of the kerogen property used to construct the model, e.g., from a set of samples where the kerogen property has been measured, can also be represented by a range of values, where the range of values includes representing uncertainty in the measured kerogen property. One range of values can be a distribution function. For example, vitrinite reflectance measurements, used to determine thermal maturity of kerogen, provide a histogram for a given sample, where individual populations in the histogram represent the different reflectance of vitrinite macerals that are present in the sample, for example due to random orientation of the macerals. A mean value of vitrinite reflectance can be determined from these populations, and a standard deviation from the mean can also be determined. The range of values can be a distribution function which is used to represent the thermal maturity of each sample in the set of samples. For instance, the distribution function can be a Gaussian function, where the mean value of the population of the histogram is used as the mean value of the Gaussian function, and the standard deviation from the mean value of the population of the histogram is used as the standard deviation in the Gaussian function. The distribution function is not limited to a Gaussian function, and other functions can be used, such as a lognormal distribution, which could be advantageous because it disallows negative values.

Another embodiment of spectral interpolation is integration. For example, to determine a value representing a given vibrational mode by integration, the spectral intensity values over a spectral window for a given vibrational mode can be summed. The summed value can be used as a value that represents the vibrational mode.

Models for Estimation of Kerogen Properties

Models for determining an estimated value of a kerogen property, such as thermal maturity and density, with and without uncertainties are provided herein. Generally, a model can be determined using simple regression or a stochastic regression from the series of collected samples. The series of collected samples are measured using IR spectroscopy to determine one or more values representing one or more vibrational modes, and also measured using an independent measurement, e.g., independent of IR spectroscopy, to determine a value of the kerogen property of interest, such as using vitrinite reflectance to determine a value of thermal maturity and using gas pycnometry to determine a value of density. The values representing the vibrational modes and the measured values of the kerogen property of the set of samples are used to determine the model. Once the model has been determined, an estimated value of the kerogen property in a collected sample, where the value of that property in the collected sample is unknown, can be determined by inputting values representing the vibrational modes attributed to kerogen, obtained from the IR spectrum of the collected sample, into the model. The model is advantageous because once it is obtained, there is no need for further use of independent measurements to estimate the value of the kerogen property(s) in samples where the value of property(s) is unknown. IR spectroscopy can be used to determine, for example, an estimated value for thermal maturity and/or density in a sample where that value is unknown using the models described herein. Some advantages of the IR spectroscopy method compared to conventional laboratory techniques for determining kerogen properties is that it is less expensive, faster, and portable, and is capable of determining one or more kerogen properties simultaneously.

The models described herein are determined using a value or range of values representing a vibrational mode from each sample in the set of samples used to determine the model. The models also use a value or range of values representing the vibrational mode of a sample, where a value of the kerogen property is unknown, as an input. In some embodiments, the models are determined from, and use as inputs, a value or range of values representing at least three vibrational modes. Vibrational modes that may be used are the $CH_2$ antisymmetric stretch at a wavelength ranging from about 2910 $cm^{-1}$ to about 2935 $cm^{-1}$, the $CH_3$ antisymmetric stretch at a wavelength ranging from about 2945 $cm^{-1}$ to about 2970 $cm^{-1}$, and the aromatic CH stretch at a wavelength ranging from about 3010 $cm^{-1}$ to about 3060 $cm^{-1}$. Though these are the vibrational modes most commonly used in the models described herein, additional vibrational modes, i.e., more than three vibrational modes, or other vibrational modes not described herein could be utilized provided these modes demonstrate a correlation with the kerogen property of interest.

Determination of an appropriate model may begin with the selection of a set of samples obtained from one or more subsurface formations as discussed in the Sample Collection section above.

The kerogen property(s) of each sample in the set may be determined by an independent measurement, such as through the use of vitrinite reflectance for thermal maturity and gas pycnometry for density. In embodiments of the model which do not consider uncertainty, the value used for the kerogen property may be the single measured value or the mean value determined from a population. In embodiments of the model where uncertainty is considered, a range of values (e.g., a distribution function) is used to represent the kerogen property.

The IR spectrum of each sample in the set may be measured. Optionally, the IR contributions of pure minerals and/or baseline corrections can be made to the IR spectrum if considered necessary by one of ordinary skill in the art to obtain a better spectrum on which to perform interpolation of the spectral features. Using the interpolation methods discussed herein, a value or range of values (e.g., a distribution function) which represents each vibrational mode is obtained.

From the set of values or ranges of values of the kerogen property(s) determined using independent, e.g., not IR spectroscopy, laboratory techniques or some other means, and the set of values or range of values representing the vibrational modes for the set of samples, a relationship is determined between the values of kerogen property(s) and the values representing the vibrational modes. This relationship can be determined by simple regression or stochastic regression to determine a function which best fits the data provided. For example, either regression begins by selecting a function to fit the data. For instance, this function can be any suitable function which can fit the data, such as a linear function, quadratic function, power function, and the like. One function that can be used is the following:

$$m_i = \alpha_0 + \sum_{i=1}^{S} \alpha_i \cdot s_i \quad \text{(Eq. 1)}$$

In Equation 1, $m_i$ is, for example, a value for thermal maturity (here in units of % Ro) or kerogen density, $s_i$ is a value of the $i^{th}$ vibrational mode (in arbitrary spectral units), $\alpha_i$ is a value of the $i^{th}$ coefficient which is to be determined from the regression, and S is the number of vibrational modes used in the function, where S≥1.

Simple Regression Model

When a simple regression is used, $s_i$ for the $i^{th}$ vibrational mode is a single value, such as the value of the polynomial function at the midpoint of the spectral window. In some embodiments, when at least three vibrational modes are used, $s_i$, $s_2$, and $s_3$ are the values of the polynomial function at the midpoint of the spectral windows that represent the $CH_2$ antisymmetric stretch, the $CH_3$ antisymmetric stretch, and the aromatic CH stretch, respectively. In other embodiments, when at least two vibrational modes are used, $s_i$ includes values that represent the $CH_2$ antisymmetric stretch and the $CH_3$ antisymmetric stretch. In yet other embodiments, when at least one vibrational mode is used, $s_i$ includes a value that represents the aromatic CH stretch. Single values representing each vibrational mode have been discussed herein above.

A simple regression may be performed based on the thermal maturities obtained by vitrinite reflectance and the values of the polynomial functions representing the vibrational modes for the set of collected samples to determine the values of the coefficients, $\alpha_i$. A simple regression may be performed based on the kerogen densities obtained by gas pycnometry or the like and the values of the polynomial functions representing the vibrational modes for the set of collected samples to determine the values of the coefficients, $\alpha_i$. Simply put, a function which represents the best-fit of the values of the kerogen properties(s) and the values of the polynomial functions representing the vibrational modes is obtained. In this example, the best-fit function is a linear function that uses values of the polynomial functions representing vibrational modes as an input and estimated value of the kerogen property as an output.

This best-fit function is the basis of a model which can be used to estimate the value of the kerogen property in a sample where the value of the property is unknown. For example, the sample can be measured using IR spectroscopy, and the values of the polynomial functions representing the vibrational modes are determined in the same way that these values were determined for each sample in the set of samples, i.e., the same spectrum window, the same types of polynomial functions, etc. If the kerogen property is thermal maturity, then it is determined by using these values representing vibrational modes as inputs in the model and calculating the estimated value of thermal maturity as an output. In this manner, an estimated value of thermal maturity of a sample having an unknown value of thermal maturity can be made, but without having to measure the thermal maturity of the sample using the more expensive vitrinite reflectance technique. Similarly, if the kerogen property is kerogen density, then it is determined by using the values representing vibrational modes as inputs in the model and calculating an estimated value of the kerogen density as an output. In this manner, an estimated value of kerogen density of a sample having an unknown value of density can be made, but without having to measure the density of the sample using more time-consuming and expensive laboratory methods such as gas pycnometry on isolated kerogen.

Stochastic Model

A model which factors in uncertainty in the values of the kerogen properties and in the values representing the vibrational modes can also be used. Similar to simple regression, this model can use at least one vibrational mode, at least two vibrational modes, at least three vibrational modes or a plurality of vibrational modes to estimate thermal maturity.

The model differs from the model without uncertainty in that a simple regression is replaced with a stochastic regression technique such as Bayesian Monte-Carlo regression. In addition, the thermal maturities and values representing the vibrational modes are represented as a range of values, such as probability distributions, and not simply as single values, e.g., mean values. As discussed herein, the spectral values representing the vibrational modes can be represented by a range of values, such as probability distribution functions (e.g., Gaussian function), where the residual spectrum between the measured IR spectrum and the fitted polynomial function is used to represent uncertainty. Thermal maturities obtained by vitrinite reflectance and densities obtained by gas pycnometry can also be represented by a range of values, such as distribution functions, as discussed herein.

From the sets of range of values, such as distribution functions, used to represent the values and uncertainties for the kerogen property(s) and the sets of range of values, such as distribution functions, representing the vibrational modes of the set of samples, a relationship is determined between the values of the kerogen property(s) and the values representing the vibrational modes. This relationship may be determined by stochastic regression to determine a function which best fits the data provided. Similar to the simple regression, the stochastic regression begins by selecting a function to fit the data obtained from the set of samples. As discussed herein, several types of functions can be utilized, such as linear, quadratic, power, logarithmic, and the like. For example purposes, the stochastic regression will also be discussed using Equation 1, which is a linear function. Generally, the goal of the stochastic regression is the same as that of the simple regression, i.e., to determine a function which best fits the available data by determining the values of $\alpha_i$ in e.g., Equation 1. However, the difference between simple regression and the stochastic regression is that stochastic regression uses ranges of values, such as distribution functions, to represent the kerogen property(s) and the vibrational modes to determine a range of values, e.g. a distribution, for the coefficients $\alpha_i$, where the range of values includes values representing uncertainty in the $\alpha_i$. An example application of stochastic regression for evaluating a distribution of the $\alpha_i$ from distributions of the kerogen property and the vibrational modes is provided by the following likelihood function representing the distribution of the $\alpha_i$ :

$$L(\alpha) \propto \exp\left[-\sum_{j=1}^{N}\frac{1}{2\sigma^2}\left(\alpha_0+\alpha_1 s_1^{(j)}+\alpha_2 s_2^{(j)}+\alpha_3 s_3^{(j)}-\mu^{(j)}\right)^2-\sum_{j=1}^{N}\sum_{i=1}^{3}\frac{1}{2\sigma_j^2}\left(s_i^{(j)}-\mu_i^{(j)}\right)^2\right] \quad \text{(Eq. 2)}$$

For example, the estimated range of values kerogen property can be represented by a normal distribution with mean $\mu$ and variance $\sigma^2$, and the estimated range of values representing the vibrational modes can be normal distributions with mean $\mu_i$ and variance $\sigma_i^2$. Random samples of the $\alpha_i$ are then drawn from the probability density function $L(\alpha)$. These samples of the $\alpha_i$ may then be used to estimate the distribution of the $\alpha_i$.

This best-fit function (i.e., Equation 1 with the distribution of the $\alpha_i$ determined by stochastic regression) is the basis of a model which can be used to estimate values of kerogen property(s), such as thermal maturity and density, of a sample having unknown values for the property(s). For example, the sample is measured using IR spectroscopy, and distribution functions which represent each of the vibration modes are determined in the same way that these distribution functions were determined for each sample in the set of samples, i.e., the same spectrum windows, the same types of polynomial functions, etc. The kerogen property is then determined by stochastic simulation, such as a Monte Carlo simulation. For example, a series of simulations is run using random values selected from the distribution functions representing the vibrational modes of the sample having unknown values of the kerogen property(s) and random values selected from distribution functions representing the coefficients $\alpha_i$. From these random values a series of estimated values of the kerogen property(s) is determined from the model. A histogram of these estimated values can be used to estimate a distribution function representing the uncertainty in the property(s) estimate. The number of simulations in the series may be chosen large enough to ensure a reasonable estimate of the distribution of the property. For example, after the simulations are complete, a mean value and standard deviation could be determined from the series of thermal maturities and/or densities that are calculated.

Figure 7A:
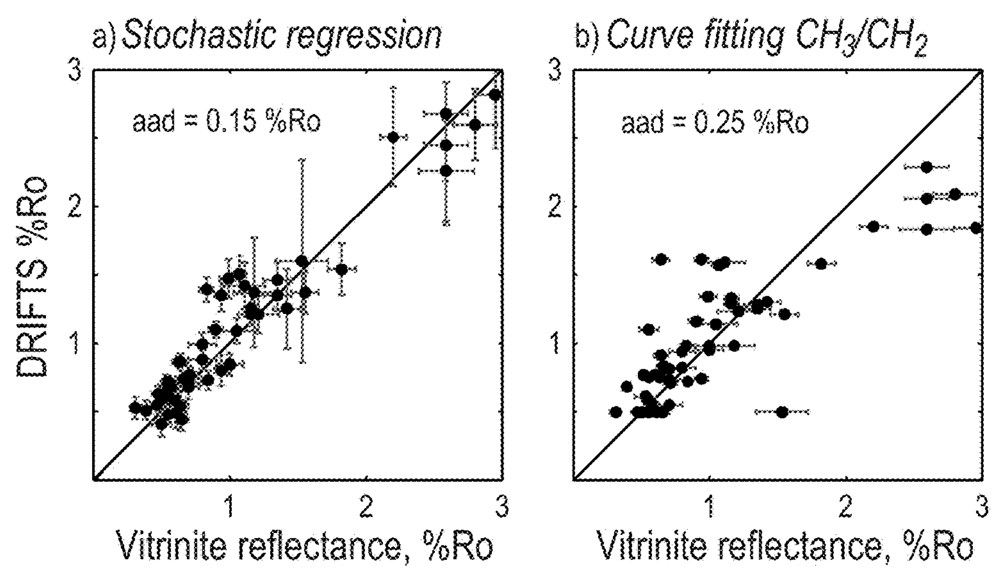
FIG. 7*a* is a comparison of thermal maturity determined using vitrinite reflectance measurements to that estimated from DRIFTS using a stochastic regression model for samples having a range of thermal maturities.

FIG. 7a depicts thermal maturities estimated from a stochastic regression model compared to those from vitrinite reflectance with their respective uncertainties for a large set of mudstone samples. The average absolute difference (aad) between thermal maturities determined using vitrinite reflectance and those determined from the stochastic regression model is 0.15 Ro. For comparison, FIG. 7b depicts thermal maturities estimated using conventional curve fitting techniques, which shows larger scatter and underestimates, in particular, thermal maturity at higher values. The aad for this set of samples based on curve fitting for the $CH_3/CH_2$ ratio is 0.25 Ro, which is nearly twice as large as from the stochastic regression model. Moreover, the curve fitting approach has no estimate of the uncertainty in the % Ro estimate.

Figure 8A:
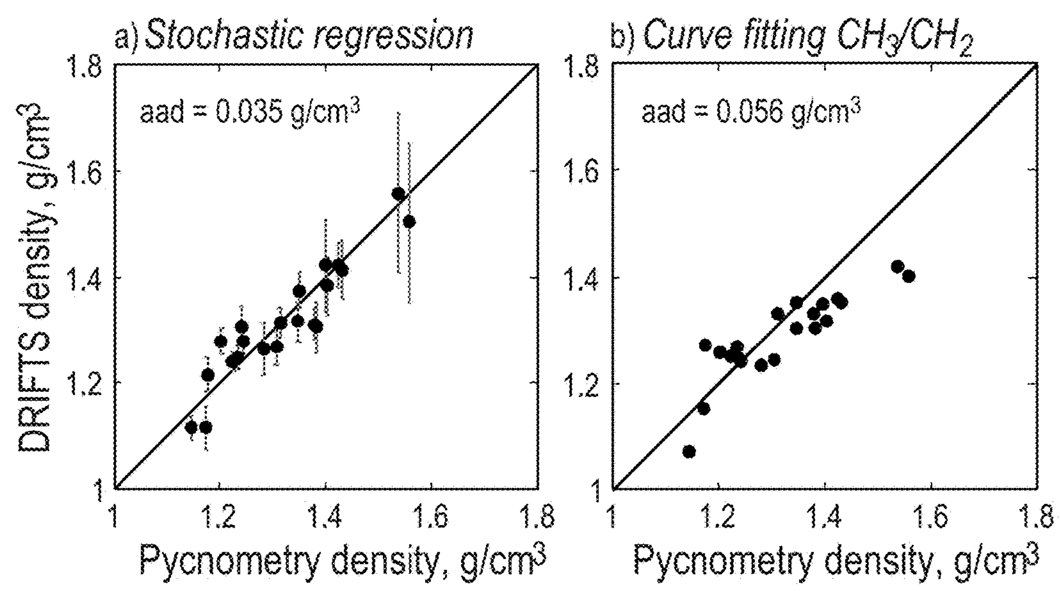
FIG. 8*a* is a comparison of kerogen densities determined using gas pycnometry measurements to that estimated from DRIFTS using a stochastic regression model for samples having a range of densities.

FIG. 8a depicts kerogen densities estimated from a stochastic regression model with their respective uncertainties compared to those from gas pycnometry for a large set of mudstone samples. The average absolute difference (aad) between density determined using pycnometry and those determined from the stochastic regression model is 0.035 g/cm$^3$. For comparison, FIG. 8b depicts kerogen densities estimated using conventional curve fitting techniques, which shows larger scatter and underestimates, in particular, density at higher values. The aad for this set of samples based on curve fitting for the $CH_3/CH_2$ ratio is 0.056 g/cm$^3$, which is step larger than from the stochastic regression model. Moreover, the curve fitting approach has no estimate of the uncertainty in density estimate.

Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only certain examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The invention claimed is:

1. A method for estimating a value of a kerogen property in a subsurface formation, the value of the kerogen property being unknown, the method comprising:

measuring spectral intensity values over an infrared (IR) spectral range for a selected sample from the subsurface formation;

determining a range of values representing the measured spectral intensity values corresponding to a vibrational mode attributable to kerogen in the selected sample, the range of values including values representing uncertainty in the measured spectral intensity over a portion of the spectral range; and inputting values from the range of values into a stochastic regression model to determine an estimated value of the kerogen property in the selected sample; and wherein the measured spectral intensity values are attributable to a plurality of vibrational modes attributable to kerogen in the selected sample, the determining step further comprising:

for each vibrational mode in the plurality of vibrational modes, determining a range of values representing the measured spectral intensity values corresponding to the vibrational mode, the range of values including values representing uncertainty in the measured spectral intensity;

and the inputting step further comprising:

for each vibrational mode in the plurality of vibrational modes, inputting values from the range of values into the stochastic regression model to determine the estimated value of the kerogen property in the selected sample.

2. The method of claim 1, wherein the plurality of vibrational modes are selected from a group consisting of: a $CH_2$ symmetric stretch, a $CH_2$ antisymmetric stretch, a $CH_3$ symmetric stretch, a $CH_3$ antisymmetric stretch, a CH stretch, an aromatic CH stretch, and combinations thereof.

3. The method of claim 1, wherein the stochastic regression model is based on a relationship determined from a first set of range of values and a second set of range of values, a range of values from the first set representing measured values of a kerogen property determined from a sample in a set of samples from one or more subsurface formations, the range of values from the first set including values representing uncertainty in the measured values of the kerogen property, a range of values from the second set representing the measured spectral intensity values corresponding to the vibrational mode attributable to kerogen in a sample from the set of samples, the range of values from the second set including values representing uncertainty in the measured spectral intensity of the vibrational mode.

4. The method of claim 3, wherein the relationship is determined from a selected function using stochastic regression.

5. The method of claim 4, wherein the relationship is a set of coefficients for the selected function that relates the first set of range of values to the second set of range of values, each coefficient including a range of values, the range of values for each coefficient including values representing uncertainty of said coefficient based on the uncertainties in the measured value of the kerogen property and in the measured spectral intensity from the set of samples.

6. The method of claim 5, wherein the stochastic regression model is a simulation model which uses the set of coefficients and the range of values representing the spectral intensity of the vibrational mode of the selected sample to determine the estimated value of the kerogen property in the selected sample, wherein the estimated value includes a range of values, the range of values including values representing uncertainty in the estimated property based on the uncertainties in the set of coefficients and the measured spectral intensity from the selected sample.

7. The method of claim 5, where the inputting step further comprises:

(1) selecting one or more values from the range of values representing the measured spectral intensity values for the selected sample;

(2) selecting one or more values from the range of values for each coefficient of the stochastic regression model;

(3) inputting the selected values into the stochastic regression model to determine the estimated thermal maturity of the kerogen in the selected sample; and repeating steps (1) through (3) to determine a range of values for the estimated kerogen property.

8. The method of claim 4, wherein selected function is a linear function represented by the following equation:

$$m = \alpha_0 + \sum_{i=1}^{S} \alpha_i \cdot s_i$$

wherein m is for a value for the kerogen property, $s_i$ is a value representing a spectral intensity value of the $i^{th}$ vibrational mode, $\alpha_i$ is a value representing the $i^{th}$ coefficient determined from the stochastic regression, and wherein $S \geq 1$.

9. The method of claim 1, wherein the determining step further comprises:

fitting a polynomial function to the spectral intensity values within the portion of the spectral range of the IR spectrum corresponding to the vibration mode; and determining the range of values based on the polynomial function and a difference between values of the polynomial function and the measured IR spectrum over the portion of the spectral range.

10. The method of claim 1, where the inputting step further comprises:

(1) selecting one or more values from the range of values representing the measured spectral intensity values for the selected sample;

(2) selecting one or more values from the range of values for the coefficients of the stochastic regression model (3) inputting the values into the stochastic regression model to determine the estimated property of the kerogen in the selected sample; and repeating steps (1) through (3) to determine a range of values for the estimated kerogen property.

11. The method of claim 1, wherein the kerogen property is selected from the group consisting of: thermal maturity and density.

12. A method for estimating a value of a kerogen property in a subsurface formation, the value of the kerogen property being unknown, the method comprising:

measuring spectral intensity values over an infrared (IR) spectral range for a selected sample from the subsurface formation;

determining a value representing the measured spectral intensity value over a portion of the spectral range corresponding to a vibrational mode attributable to kerogen in the selected sample;

inputting the value into a regression model to determine the estimated value of the kerogen property in the selected sample; and wherein measured spectral intensity values include a plurality of vibrational modes attributable to kerogen in the selected sample, the determining step further comprising:

for each vibrational mode in the plurality of vibrational modes, determining the value representing the measured spectral intensity value over the portion of the spectral range corresponding to the vibrational mode attributable to kerogen in the selected sample, and wherein the inputting step further comprises:

for each vibrational mode in the plurality of vibrational modes, inputting the value into the regression model to determine the estimated value of the kerogen property in the selected sample.

13. The method of claim 12, wherein the one or more portions of the spectral range do not overlap.

14. The method of claim 12, wherein the vibrational modes are, independently selected from the group consisting of: a $CH_2$ symmetric stretch, a $CH_2$ antisymmetric stretch, a $CH_3$ symmetric stretch, a $CH_3$ antisymmetric stretch, a CH stretch, and an aromatic CH stretch.

15. The method of claim 12, wherein the regression model is based on a relationship being determined from a first set of values and a second set of values, a value in the first set representing a measured value of the kerogen property determined from a sample in a set of samples from one or more subsurface formations, a value in the second set representing the measured spectral intensity value of the portion of the spectral range from a sample in the set of samples.

16. The method of claim 15, wherein the relationship is a set of coefficients that relates the first set of values to the second set of values.

17. The method of claim 12, wherein the determining step further comprises:

fitting a polynomial function to the spectral intensity values within each portion of the spectral range; and determining the value for each portion of the spectral range based on the polynomial function.

18. The method of claim 12, wherein the determining step further comprises:

summing the measured spectral intensity values within each portion of the spectral range, wherein the summed value of the measured spectral intensity values for each portion of the spectral range is the value.

19. The method of claim 12, wherein the kerogen property is selected from the group consisting of: thermal maturity and density.

20. A method for estimating a value of a kerogen property in a subsurface formation, the value of the kerogen property being unknown, the method comprising:

measuring spectral intensity values over an infrared (IR) spectral range for a selected sample from the subsurface formation;

determining a first value representing the measured spectral intensity values corresponding to a first vibrational mode attributable to kerogen in the selected sample, the first vibrational mode is an aromatic CH stretch;

inputting the first value into a regression model to determine the estimated value of the kerogen property in the selected sample; and wherein measured spectral intensity values are attributable to a plurality of vibrational modes attributable to kerogen, the method further comprising:

determining a plurality of values representing the measured spectral intensity values corresponding to a vibrational mode attributable to kerogen in the selected sample, and wherein the inputting step further comprises:

inputting the plurality of values into the regression model to determine the estimated value of the kerogen property in the selected sample.

21. The method of claim 20, wherein the plurality of vibrational modes are independently selected from the group consisting of: a $CH_2$ symmetric stretch, a $CH_2$ antisymmetric stretch, a $CH_3$ symmetric stretch, a $CH_3$ antisymmetric stretch, or a CH stretch.

22. The method of claim 20, wherein the regression model is based on a relationship being determined from a first set of values and a second set of values, a value in the first set representing a measured value of the kerogen property determined from a sample in a set of samples from one or more subsurface formations, a value in the second set representing the measured spectral intensity value of the vibrational modes from a sample in the set of samples.

23. The method of claim 22, wherein the relationship is a set of coefficients that relates the first set of values to the second set of values.

24. The method of claim 23, wherein the regression model uses the set of coefficients determined and the values representing the spectral intensity of the vibrational modes to determine the estimate of the kerogen property in the selected sample.

25. The method of claim 20, wherein the determining step further comprises:

fitting a polynomial function to the spectral intensity values representing each of the vibrational modes within a spectral range; and determining the value representing the spectral intensity for each of the vibrational modes based on the polynomial function.

26. The method of claim 20, wherein the kerogen property is selected from the group consisting of: thermal maturity and density.

* * * * *